(12) United States Patent
Caillouette

(10) Patent No.: US 7,666,148 B1
(45) Date of Patent: *Feb. 23, 2010

(54) VAGINAL MOISTURE SCREENING ENHANCEMENT

(76) Inventor: James C. Caillouette, 685 Oak Knoll Cir., Pasadena, CA (US) 91106

( * ) Notice: Subject to any disclaimer, the term of this patent is extended or adjusted under 35 U.S.C. 154(b) by 21 days.

This patent is subject to a terminal disclaimer.

(21) Appl. No.: 11/788,010

(22) Filed: Apr. 19, 2007

(51) Int. Cl.
A61B 10/00 (2006.01)
B65D 81/00 (2006.01)

(52) U.S. Cl. .................. 600/572; 600/570; 600/584

(58) Field of Classification Search .............. 600/569, 600/570, 572, 573, 584
See application file for complete search history.

(56) References Cited

U.S. PATENT DOCUMENTS

| | | | |
|---|---|---|---|
| 4,448,205 A * | 5/1984 | Stenkvist ............... 600/562 |
| 4,981,143 A * | 1/1991 | Sakita et al. ........... 600/570 |
| 5,762,614 A | 6/1998 | Caillouette |
| 5,782,801 A | 7/1998 | Caillouette |
| 5,827,200 A | 10/1998 | Caillouette |
| 5,916,176 A | 6/1999 | Caillouette |
| 6,013,036 A | 1/2000 | Caillouette |
| 6,019,734 A * | 2/2000 | Parkinson ............... 600/572 |
| 6,117,090 A | 9/2000 | Caillouette |
| 6,390,991 B1 | 5/2002 | Caillouette |
| 6,406,441 B1 | 6/2002 | Caillouette |
| 6,544,196 B2 | 4/2003 | Caillouette |
| 7,101,342 B1 * | 9/2006 | Caillouette ............. 600/551 |

* cited by examiner

*Primary Examiner*—Max Hindenburg
*Assistant Examiner*—Jonathan M Foreman
(74) *Attorney, Agent, or Firm*—William W. Haefliger

(57) ABSTRACT

Apparatus for quick screening for vaginal moisture pH level and for amine associated with such moisture, comprising a manipulable element including a probe insertable into the vagina; a pH indicator on a first side of the element, the indicator characterized as producing a color which corresponds to pH level of vaginal moisture contacting the indicator; and a second indicator on a second side of the element, the second indicator elongated lengthwise of the element and being an amine indicator, the second indicator having an outer surface exposed to vaginal moisture, the surface presenting a sequence of crests for collection of moisture between crests in response to movement of the element in the vagina.

37 Claims, 9 Drawing Sheets

VAGINAL MOISTURE SCREENING ENHANCEMENT

BACKGROUND OF THE INVENTION

This invention relates generally to screening of vaginal moisture for amine associated with such moisture, and more particularly to enhancement of collection of such moisture to enable such screening. Also, the invention relates to related screening for moisture pH level.

There is need for enhancement of both aspects of such screening, and particularly to enhanced moisture collection to enable efficient screening for amine presence as where amine detection is carried out externally of the vagina. Also there is need for a rapid, easily performed method of such testing, or obtaining such measurement, as on a preliminary rapid basis. Also, such need relates to multiple purpose screening of vaginal moisture.

There is continued need to obtain pH measurement of vaginal fluid, as for example in the determination of whether amniotic fluid has escaped into the vagina, during late pregnancy; another example is testing to determine need for estrogen therapy. There is also need for quick, simple test determination that positively alerts the user to possible problems indicated by changed conditions in the vagina as for example amine presence in vaginal moisture.

SUMMARY OF THE INVENTION

It is a major object of the invention to provide apparatus and method to meet the above needs. A further object is to provide a method for quick screening for vaginal moisture pH level and for amine associated with such moisture, comprising a) providing a manipulable element including a probe insertable into the vagina, b) providing a pH indicator on a first side of said element, said indicator characterized as producing a color which corresponds to pH level of vaginal moisture contacting the indicator, c) providing a second indicator on a second side of said element, said second indicator elongated lengthwise of said element and being an amine indicator, d) and providing said second indicator with an outer surface exposed to vaginal moisture, said surface presenting a sequence of crests for collection of moisture between the crests in response to movement of the element in the vagina.

As will be seen, the method typically may include manipulating the probe to effect collection of vaginal moisture concentrations on the second indicator outer surface and between surface crests. The indicator crested surface may incorporate an hydroxide, or hydroxide may be applied to that surface externally of the vagina, and particularly to moisture enhanced collection zones between the crests. Efficiency of detection of the presence of amine or amines at the enhanced collection zones is thereby increased.

Another object is to provide said crests to extend either widthwise or generally lengthwise of the indicator, or both widthwise and lengthwise, for enhanced moisture collection, and to provide crests and valleys between the crests as an undulating moisture collection surface or surfaces. The indicator may be provided in the form of a probe surface, or a strip of material adherent to the probe, with an outer surface formed as undulating in the direction of probe manipulated movement longitudinally and/or laterally in the vagina.

An added object is to provide apparatus for quick screening for vaginal moisture pH level and for amine associated with such moisture, comprising a) a manipulable element including a probe insertable into the vagina, b) a pH indicator on a first side of that element, said indicator characterized as producing a color which corresponds to pH level of vaginal moisture contacting the indicator, c) and a second indicator on a second side of the element, said second indicator elongated lengthwise of said element and being an amine indicator, d) said second indicator having an outer surface to be exposed to vaginal moisture, said surface presenting a sequence of crests for collection of said moisture between the crests in response to movement of the element in the vagina, hydroxide being exposed to collected moisture.

Another object includes the provision of a carrier for said hydroxide, and manipulating said carrier to effect said application of the hydroxide to a vaginosis test site after moisture enhanced collection thereon. The carrier may in the regard be provided in the form of an easily manipulated ampule, which may be initially located on a support for the probe, the assembly being in kit form.

A further object includes provision of a vaginosis test site in elongated and multiple crested form at one side of the probe, that site typically consisting of an absorbent material, examples being "waste lock" from M2 polymer, or highly absorbent "Lyocell Fiber" disclosed in "Medical Textiles", June 2003, page 3.

Test sites on the probe are preferably located at opposite sides of the probe, as for example in opposition to one another, enabling maximum site area for collection and exposure to moisture, enhancing use efficiency as by a "whiff test" for amine or as a diagnostic device.

An additional object includes selection of the hydroxide from the group:
i) KOH,
ii) milk of magnesia,
iii) sea water,
iv) baking soda, or mixture thereof with water.

Yet another object includes provision of the pH test, to include
i) a pH indicator characterized as producing a color which corresponds to pH level of vaginal moisture contacting the indicator,
ii) a local comparison zone having a color corresponding to a predetermined pH level, and positioned and shaped for quick color comparison with the color of said indicator after indicator contact with vaginal moisture.

Another object is to provide a local comparison zone exhibiting a color which corresponds to a fixed standard, such as a predetermined pH level. That zone may be on the probe as for example in local and quick visual comparison proximity to the moisture responsive indicator.

A further object is to provide both the indicator and the color comparison zone to have substantially the same undulant sizes and shapes, for enhancement of screening visual accuracy of color comparison, especially when the color of the zone (standard) is close to the color of the indicator as driven by vaginal moisture pH.

These and other objects and advantages of the invention, as well as the details of an illustrative embodiment, will be more fully understood from the following specification and drawings, in which:

DETAILED DESCRIPTION

Figure 1:
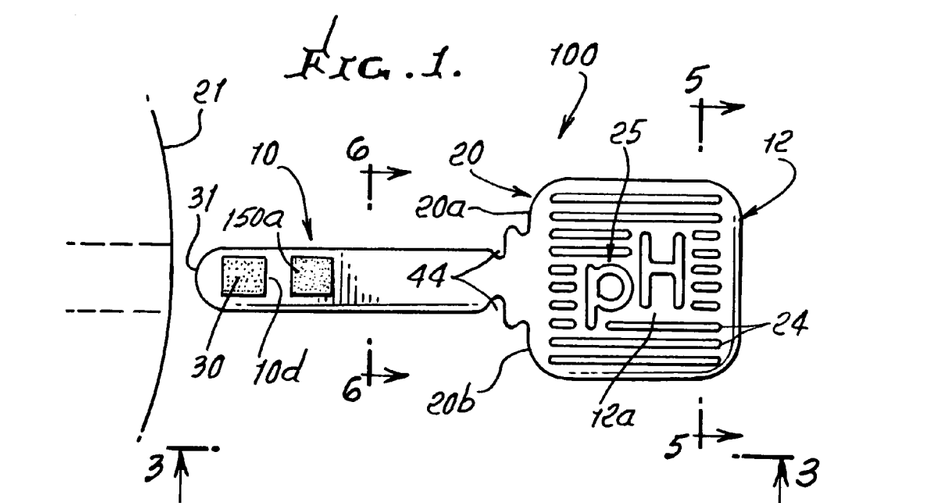
FIG. 1 is a top plan view of a probe and support.
Figure 2:
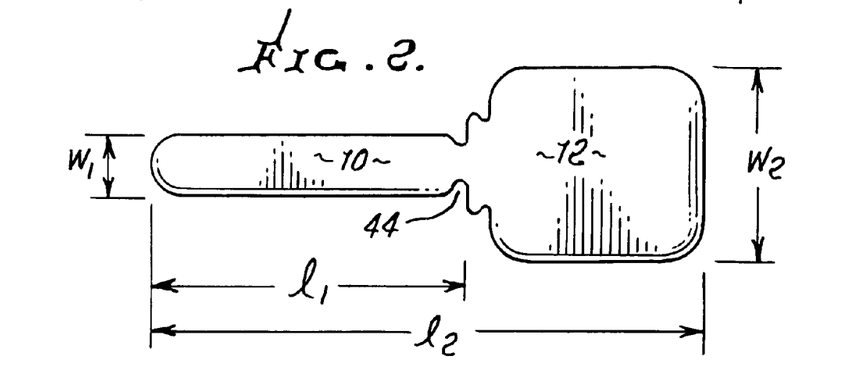
FIG. 2 is a bottom plan view of the FIG. 1 probe and support.

Referring first to FIG. 1, it shows a device that includes:

a) a longitudinally elongated probe insertable into the vagina, for a test purpose, b) a support operatively connected with the probe projecting away from the support, c) the support including:

i) a manually manipulable handle, ii) and an edge presented generally longitudinally for limiting probe insertion into the vagina.

Figure 3:
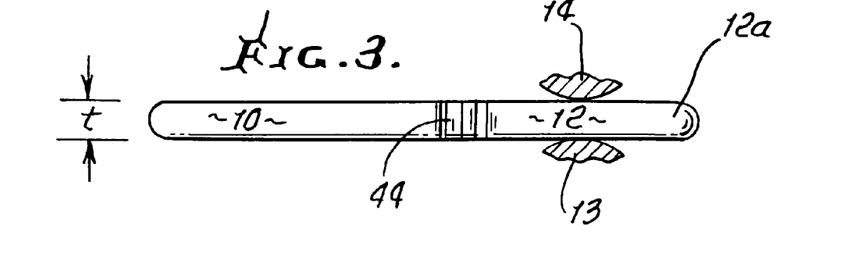
FIG. 3 is an edge view taken on lines 3-3 of FIG. 1.

As shown, the probe 10 of the apparatus 100 protrudes lengthwise from the support 12, which defines a handle 12a that can be easily gripped between the thumb 13 and forefinger 14 of the user, as seen in FIG. 3. The probe and support preferably have key-like configuration, as shown.

Forwardly or longitudinally presented edge 20 of the support limits insertion of the probe, as by engagement with the body 21, and dual edges may be provided as at 20a and 20b, at opposite lateral sides of the probe, for that purpose. The apparatus 100 may for example consist of plastic, metal or compressed fiber (example paper).

Surface irregularities may be provided on one laterally facing side of the support, and such irregularities are shown to extend longitudinally to be grasped by the thumb and prevent lateral slippage, relative to the user's thumb. The irregularities are shown in the form of protuberances 24 which are laterally spaced apart.

The probe and support, or handle may have the following dimensions for best results:

probe overall length "$l_1$"=1½ to 2½ inches probe width "$w_1$"=¼ to ½ inch support width $w_2$=¾ to 1½ inch thickness "t"=3/16 to 5/16 inch overall length $l_2$ of probe and support=3¼ to 3¾ inches.

Preferably, $l_1 \cong 2$ inches $w_1 \cong \frac{3}{8}$ inch $w_2 \cong 1\frac{1}{4}$ inch $t \cong \frac{1}{4}$ inch $l_2 \cong 3\frac{1}{2}$ inch.

Figure 6:
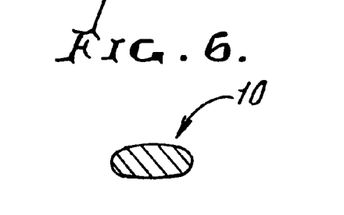
FIG. 6 is a section on line 6-6 of FIG. 1.

Also, the probe has an approximately flat, oval cross section, as seen in FIG. 6.

FIG. 1 also shows a test element or indicator 30 at the side of the probe, near its tip 31, to be pressed toward and against the vaginal wall. Element 30 typically comprises an indicator element, as for example one of the following:

i) a pH indicator ii) an amine indicator iii) a bacteria indicator iv) sialidase indicator v) prolidase indicator.

Figure 9:
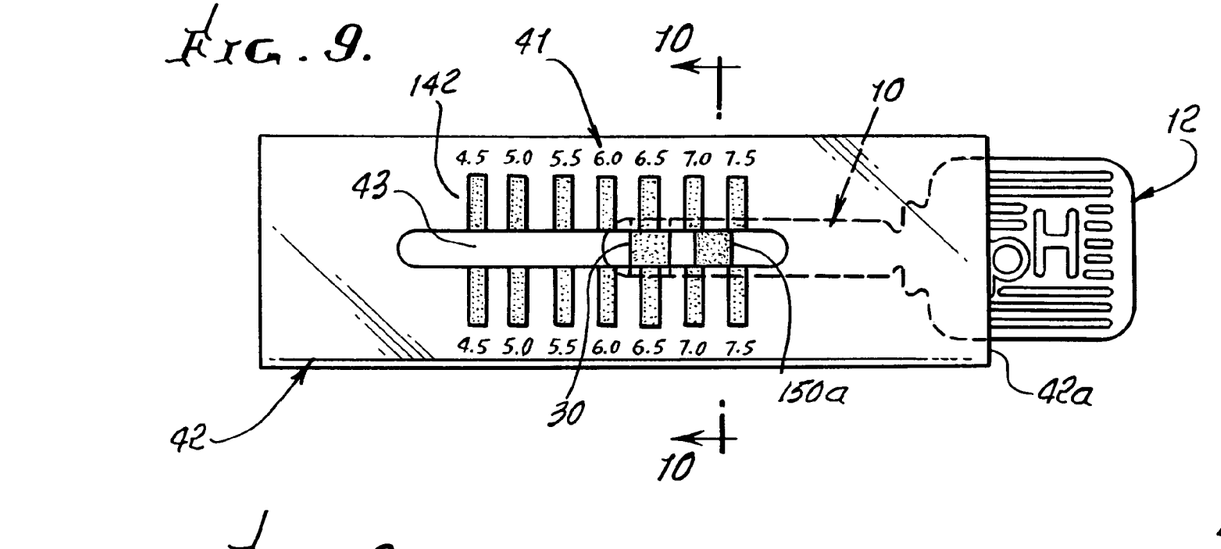
FIG. 9 is an enlarged view showing details of the sheath, with probe viewing window, and color comparison measurement zones, on the sheath; and also showing comparison of a color change of a test element with different colored zones on a sheath or other carrier.
Figure 10:
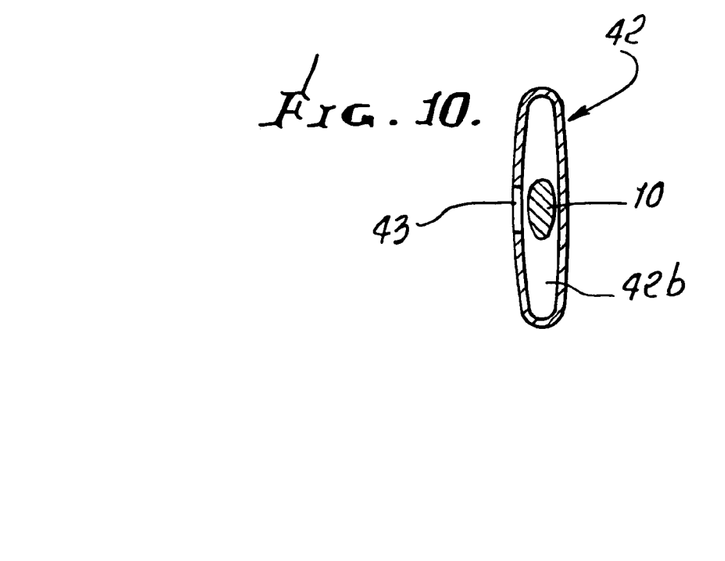
FIG. 10 is a section taken on lines 10-10 of FIG. 9.

The pH indicator or detector typically takes the form of a Nitrazine® strip or other carrier element adhered to the side of the probe, as for example by double sided adhesive tape. The outer surface of indicator 30 may be formed to be wavy, to have crests and valleys, for enhanced moisture collection, as discussed in connection with FIGS. 20a-20e herein. After exposure of the strip to vaginal moisture, its changed color (according to pH level) is compared with the series 41 of bands on a sheath 42, as seen in FIG. 9. Each band has a different color corresponding to a pH level color to which the detector strip may change. See for example the indicated pH levels 4.5, 5.0, 5.5, 6.0, 6.5, 7.0 and 7.5 adjacent the color bands.

Figure 11:
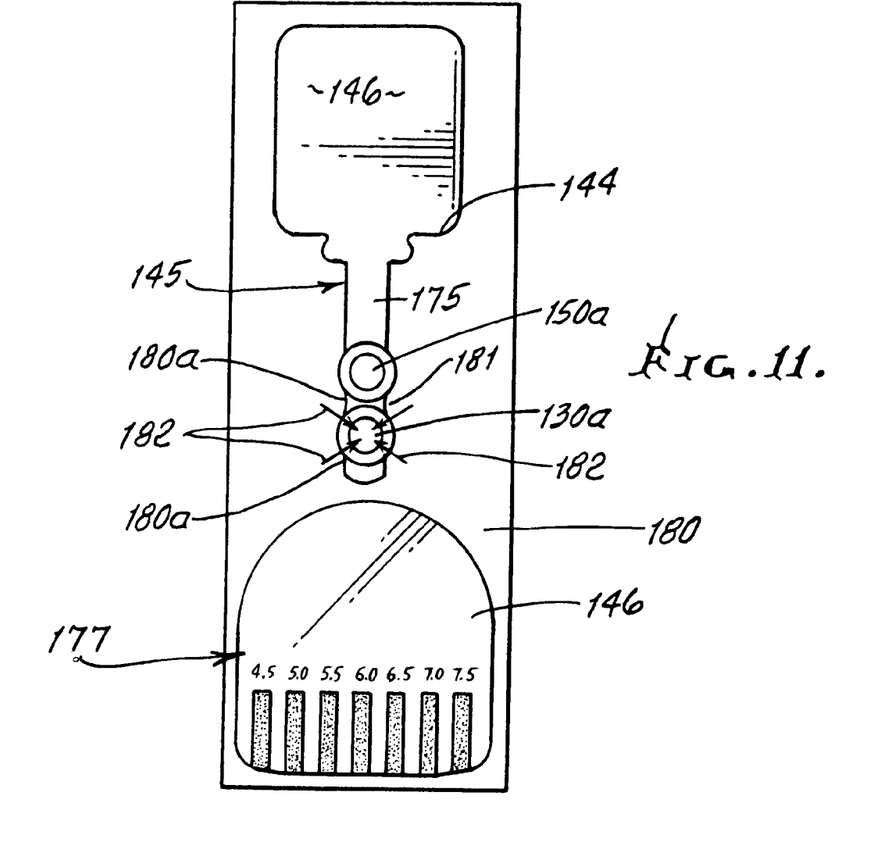
FIG. 11 is a side view of a modified apparatus.

The bands may be provided on a support strip 142 adhered to the outer surface of the sleeve or receptacle 42. See also FIG. 11 showing a manipulable element 145 including a probe 175 and handle 146 received in recesses 144 in a plastic carrier 180, with support strip 146 adhered to the carrier. A series of bands 185, like bands 41, is located on the strip 146. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue.

Figure 4:
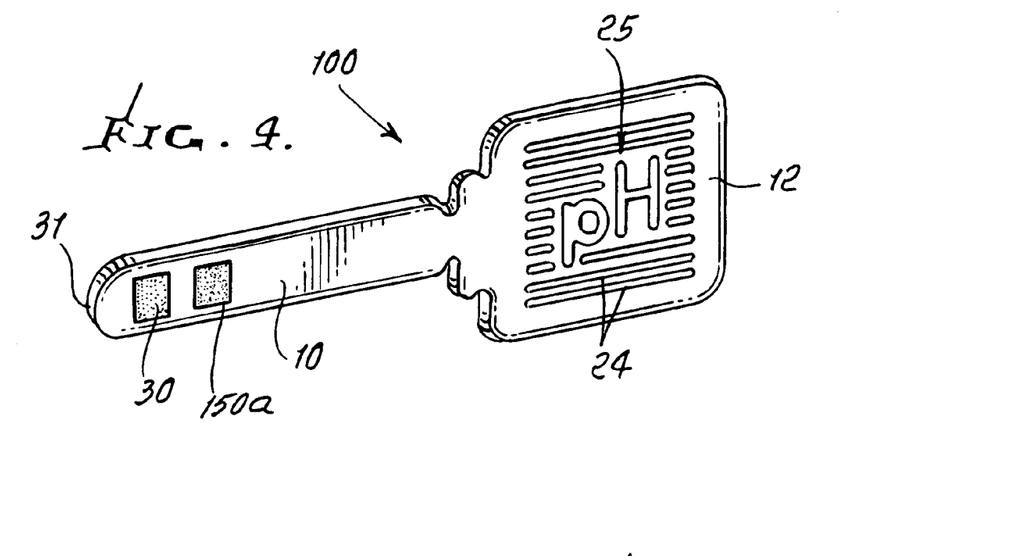
FIG. 4 is a perspective view of the FIG. 1 probe and support.
Figure 5:
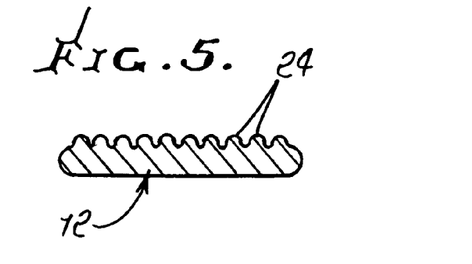
FIG. 5 is a section taken on lines 5-5 of FIG. 1.
Figure 7:
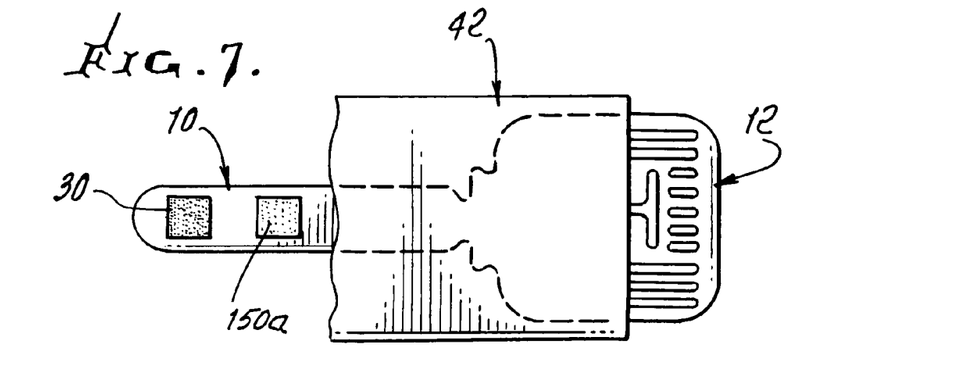
FIG. 7 is a view of the FIG. 1 probe received in a protective sheath.
Figure 8:
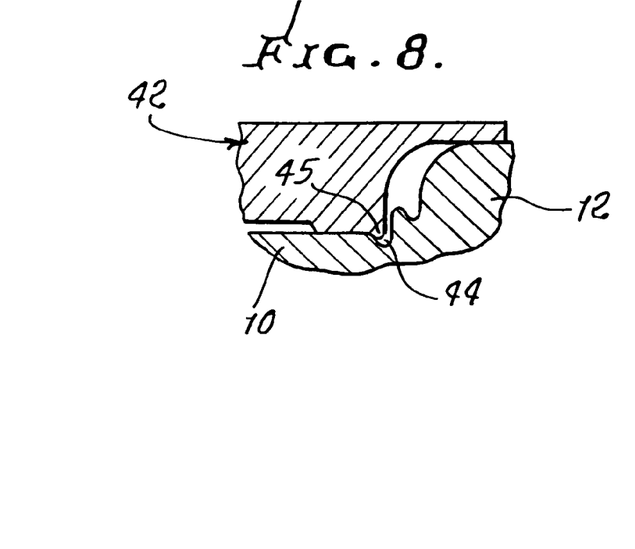
FIG. 8 is a fragmentary view showing interlocking of the sheath and probe.

In FIG. 11 a standard comparison zone is provided on the probe, one example being a plastic part 150aa received in a recess in the probe in proximity to the pH sensitive indicator 130a. The outer surface of part 150aa has a color corresponding to a predetermined pH level, at or near neutral pH level, such as 4.5 for example, for quick visual color comparison with the color of the indicator, after indicator contact with vaginal moisture. When a Nitrazine® indicator is used, the surface of part 150aa can be sunflower yellow, to indicate a standard 4.5 pH. A corresponding part 150a is shown in FIGS. 1, 4 and 7.

In use, the user first visually compares the color of the indicator 130a (after exposure to vaginal moisture) and the standard zone (such as the surface of locality 150aa), and any difference in color indicates a possible problem. This consists of a screen test. The color, size, and location of standard zone 150 are such as to provide prominent visual color comparison of zone 150aa with the indicator. Next, the probe 175 and sleeve or receptacle 180 are relatively moved, to bring the detector indicator 130a (after its exposure to moisture and color change as referred to above) into lateral registration with the color comparison bands 185, enabling ready visual comparison of the color of the detector strip with the closest color of one of the bands, enabling a pH level determination. For this purpose, a window zone of the carrier sleeve adjacent the bands may be transparent to allow visual observation of the detector, through that zone, adjacent the bands.

In summary, the probe is inserted into the vagina to collect moisture and withdrawn, and the quick visual screen comparison is made, viewing the probe indictor and the standard comparison zone for quick detection of a possible problem, as for example need for estrogen. Thereafter, color comparison may be made with the colored bands, to more definitively determine moisture pH level. The probe is re-inserted into the elongated carrier receptacle 180.

The color changing reactant may consist, for example, of one or more of the following: Bromocresol Green, Bromocresol Purple, Nitrazine Yellow, Bromophenol Blue, and equivalents.

An optional procedure consists of obtaining a visual comparison of the color changed zone on the receiver 130a with a color, or different colors, or band color shades, as at 185, where one color band may indicate presence of putrecine; another color band may indicate presence of cadaverine; and a third band may have another color or color shade close to but different from the first two, and so indicating absence of putrecine or cadaverine, or other bacterial producing amine, i.e. an amine test when compared side-by-side with the color on the receiver 130a. Such amine indicates presence of pathogenic bacteria.

In FIG. 11, the indicator 130a and comparison zone 150a have substantially the same sizes and shapes, for enhancement of visual accuracy of color comparison. Also, the probe 145 has a substantially flat side 175, the indicator and comparison zones being exposed at that flat side. The local indicator and comparison zones are located in mutual proximity lengthwise of the probe, for rapid digital type color comparison readout (i.e. problem or no problem, per color visual differentiation). Both are substantially circular, and the exposed surfaces of each extend in substantially the same flat plane. The surface of 130a may be wavy to have crests and valleys, for enhanced moisture collection, as described in FIGS. 20a-20e. The surface of 150aa may also similarly be undulant for accurate comparison with 130a. Undulant edges 180a of the carrier and/or edges of 130a to 150a allow or facilitate relative travel of moisture along multiple paths 181 to reach the indicator 130a or zone 150a. See path arrows 182. The diameters of 130a and 150a may be between 3/16 and 3/8 inch, for optimum visual comparison effect. All of these contribute to enhancement of accurate, quick, viewing comparison to quickly detect color differences from a standard level. Carrier 180 receives the probe 145 and handle 146, and carries the pH color comparison chart 177.

Figure 12:
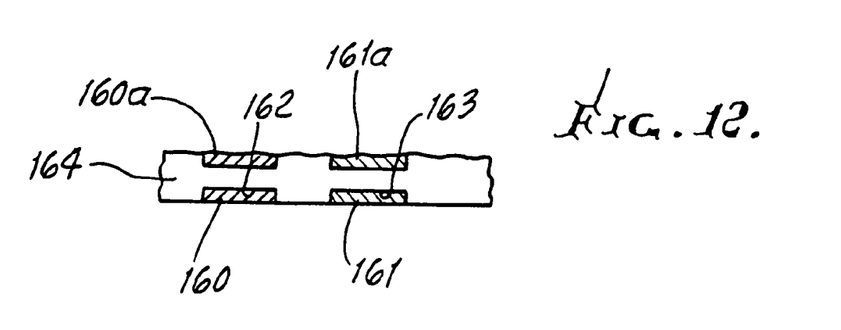
FIG. 12 is an enlarged view showing the carrying on a probe of an indicator and comparison standard, as well as of a wavy moisture collector surface.

FIG. 12 shows reception of an indictor 160 and comparison zone plastic button 161, in recesses 162 and 163 in a probe 164, the outward facing surfaces of 160 and 161 being of generally the same size and shape and in the same plane for accuracy of comparison (equal illumination, light reflections, etc.).

Vaginal conditions related to pH are indicated as follows:

| 1. | Bacterial Infection | above | 4.5-6.5 |
| 2. | Menopause | above | 4.5-6.5 |
| 3. | SPROM | above | 4.5-7.5 |
| 4. | Osteoporosis | above | 4.5-6.5 |

Additional indicators and standard comparison zones may be provided on the probe, as shown at 160a and 161a, in FIG. 12, for redundancy and color differentiation confirmation. The surfaces of both 160a and 161a may be similarly wavy or undulant for moisture gathering enhancement and observation accuracy.

U.S. Pat. No. 6,406,441 is incorporated herein, by reference.

Figure 13:
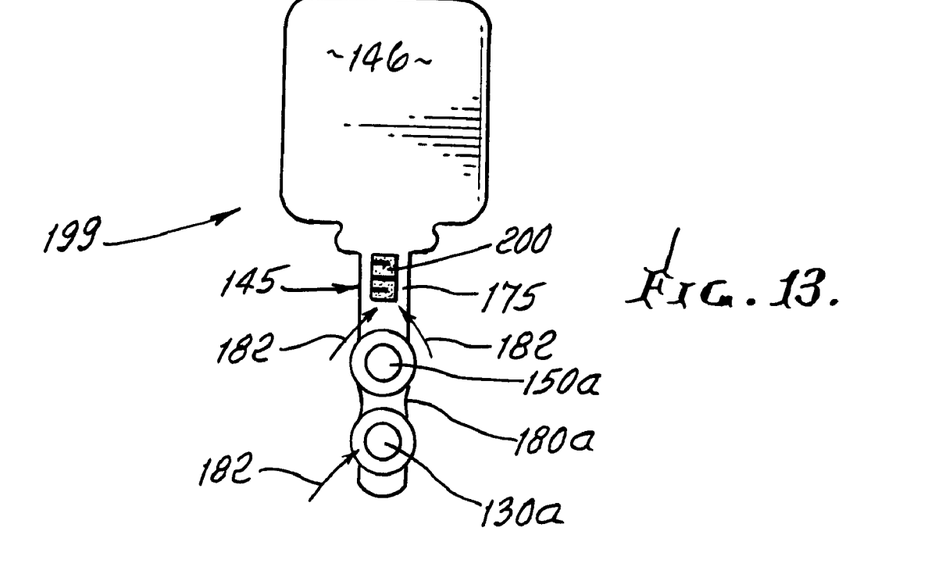
FIG. 13 is a view showing a vaginal probe with multiple test sites.

FIG. 13 shows a modification 199 in which elements the same as in FIG. 11 have the same identifying numerals. In addition, an elongated strip 200 is applied to the flat side 175 of the probe 145. Strip 200 includes, or carries, a thin layer of KOH, or other equivalent hydroxide reactive with an amine produced by vaginal bacteria, for use in testing for such an amine in the fluid sample from the vagina. See flow path arrow 182. When contacted with an amine in vaginal moisture the KOH reacts to produce a characteristic odor, which is a "fish" type odor, from which a doctor can diagnose the presence of amine in the test sample. Accordingly, the device 199 provides multiple test sites to enable quick multiple diagnostic tests for vaginal pH as may indicate estrogen deficiency as described, and for presence of amines (produced by vaginal bacteria) indicative of BV (i.e. bacterial vaginosis). Such amines include cadavarine and putrecine. The surface of 200 may be wavy as described in FIGS. 20a-20e herein, as may surfaces of 130a and 150a.

Figure 14:
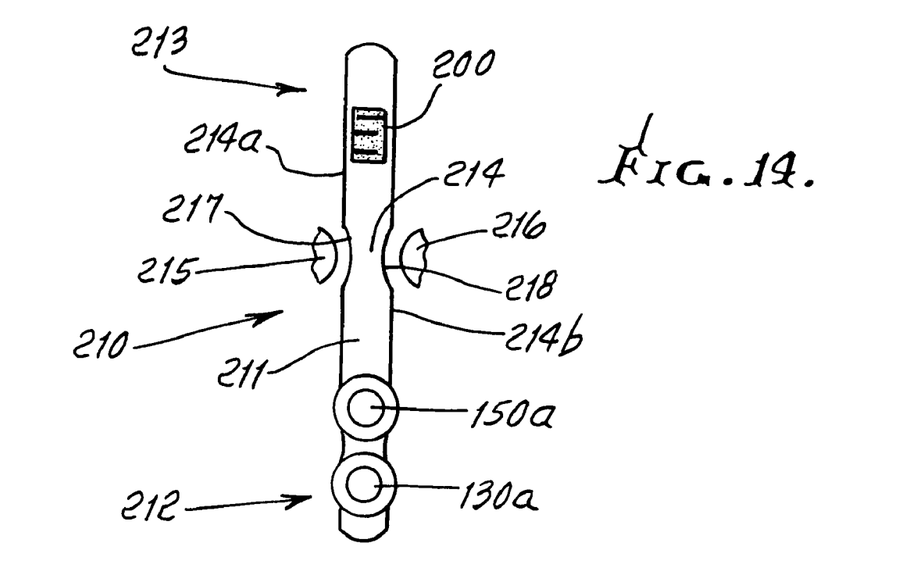
FIG. 14 shows another modification.

FIG. 14 shows a further modified device 210 which comprises an elongated thin stem 211 having test site zones 212 and 213 extending endwise oppositely of stem mid-portion 214. That mid-portion is adapted to be grasped as by the user's thumb 215 and first finger 216, during use of the device 210. There may be concave recesses 217 and 218 sunk in the edges 214a and 214b of stem mid-portion 214, for grasping and stem manipulation purposes. Test sites 130a and 150a at zone 212 are the same as provided in FIG. 13, i.e. have the same utility and relative placement.

Test site 200 has the same structure and utility as site 200 in FIG. 13; however, it is located at zone 213, remotely from sites 130a and 150a. In use the stem or stick is manipulated so that either zone 212 or zone 213 is first inserted into the vagina to receive vaginal moisture, as by moving the stem lengthwise in the vagina adjacent a layer of moisture, and subsequently the stem is withdrawn and endwise removed so that the other of the zones 212 or 213 can then be separately inserted into the vagina to receive vaginal moisture and then withdrawn. This procedure avoids contact of moisture on site 200 with moisture on sites 130a and 150a, while still enabling rapid use and observation of all test sites 130a, 150a and 200. Such contact of moisture on site 200 with moisture on either or both of sites 130a and 150a could detrimentally change the pH at those latter sites due to the pH of the hydroxide containing moisture at site 200. As an alternative, the device of FIG. 13 could be modified to place site 200 at the opposite side of the stem 175, so that moisture on site 200 would be unlikely to be displaced as by smearing to contact moisture at sites 130a and 150a, at the opposite sides of the stem.

A protective film may be applied to cover site 200 until use, as for example by application to KOH or other hydroxide at the site of vaginal discharge, i.e. applied for example by a Q-tip. The surface of 200 may be wavy, as referred to.

Figure 15:
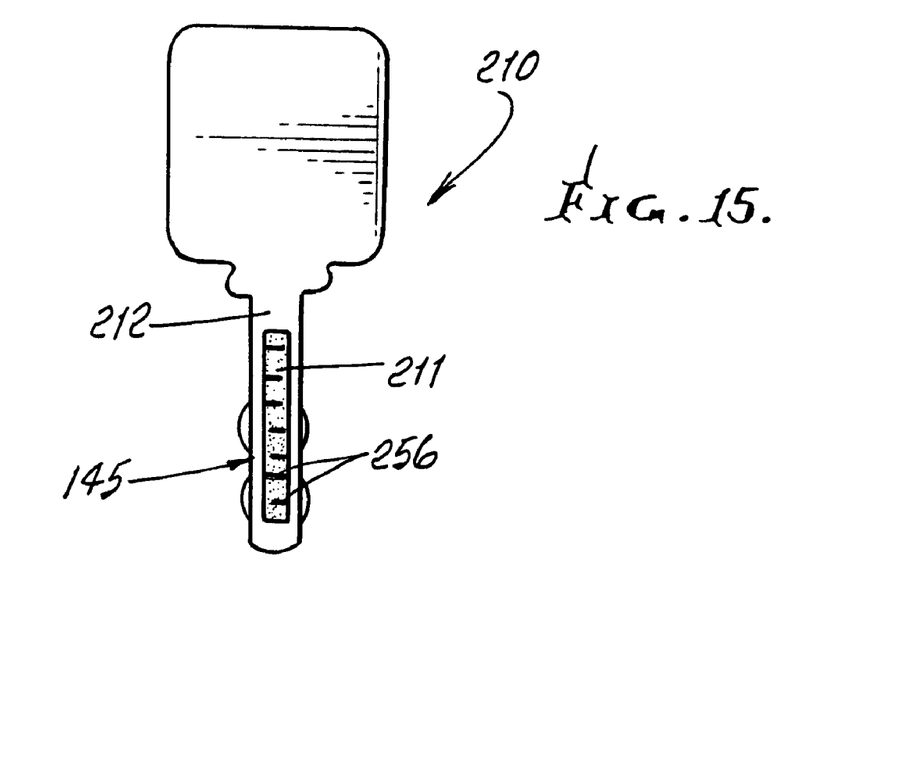
FIG. 15 shows a further modification on one side of a probe.
Figure 16:
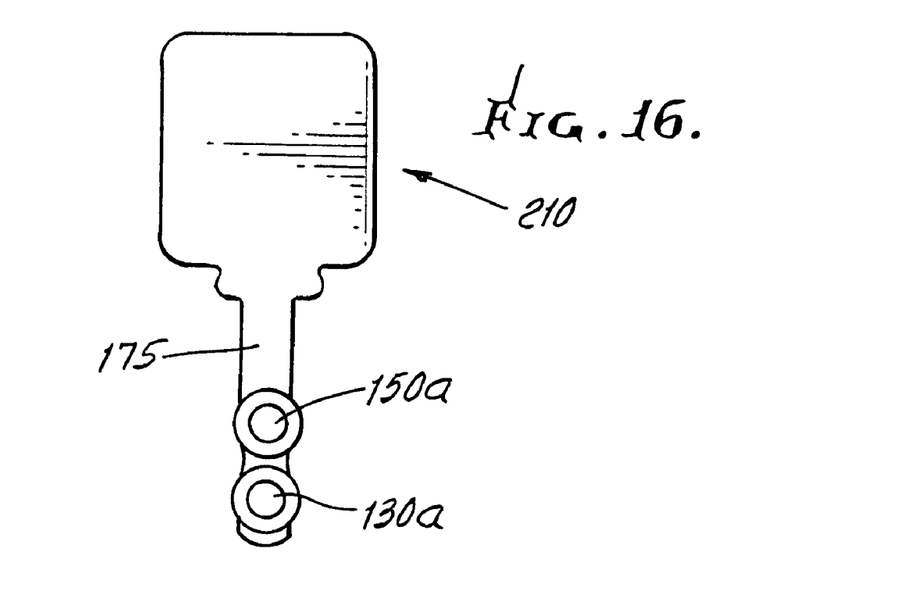
FIG. 16 shows the opposite side of the probe as seen in FIG. 15.
Figure 17:
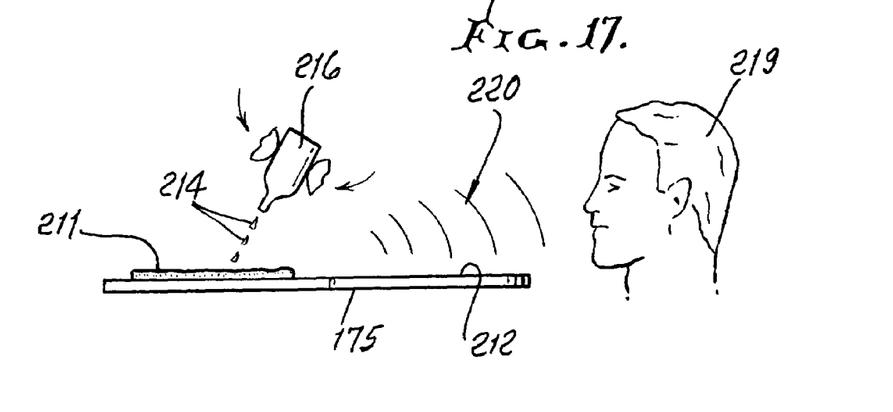
FIG. 17 shows use of the probe, as in a whiff test.

FIGS. 15 and 16 show a preferred modification 210 in which elements the same as in FIG. 11 have the same identifying numerals. In addition an elongated absorbent strip 211 is attached to the flat opposite side 212 of the probe 145, where side 212 is opposite side 175. Strip 211 has a wavy surface, as discribed in FIGS. 20a-20e herein. In use, sides 175 and 212 are exposed to moisture in the vagina, as by lengthwise movement therein, and the probe is then removed. Strip 211 constitutes a test site for production of amine or amines, such as cadaverine and putrecine. An hydroxide is then applied to the test site at moistened strip 211, externally of the vagina so contact of hydroxide with the vagina is avoided. See drops 214 of liquid hydroxide in FIG. 17, applied to strip 211, the amount of applied hydroxide being easily controllable, as by manipulation of an ampule 216.

As referred to above, when contacted with an amine in vaginal moisture, the hydroxide reacts to produce a characteristic odor, which is a "fish" type odor, from which a user 219 can detect (as seen at 220 in FIG. 17) the presence of amines in the test at the test site.

Accordingly, the device 210 provides multiple test sites to enable quick multiple diagnostic tests for vaginal pH as may indicate estrogen deficiency as described, and for presence of amine (produced by vaginal bacteria) indicative of bacterial vaginosis.

By avoiding inclusion of hydroxide on the probe at the time of insertion into the vagina, undesirable application or mixing of hydroxide with the pH test sites seen in FIG. 16 is avoided, whereby erroneous readings of pH are avoided. Strip 211 can thus be located at the direct opposite side of the probe from the pH indicators 130a and 150a, without risk of hydroxide contamination of those sites. Usable hydroxides include: KOH, milk of magnesia, baking soda and sea water, as well as others. The strip 211 may consist of a "Super Absorbent Polymer" such as "Waste Lock", from M2 Polymer, or the highly moisture absorbent "Lyocell Fiber" referenced in "Medical Textiles", June 2003, at page 3, as well as others, such as filter paper.

Figure 18:
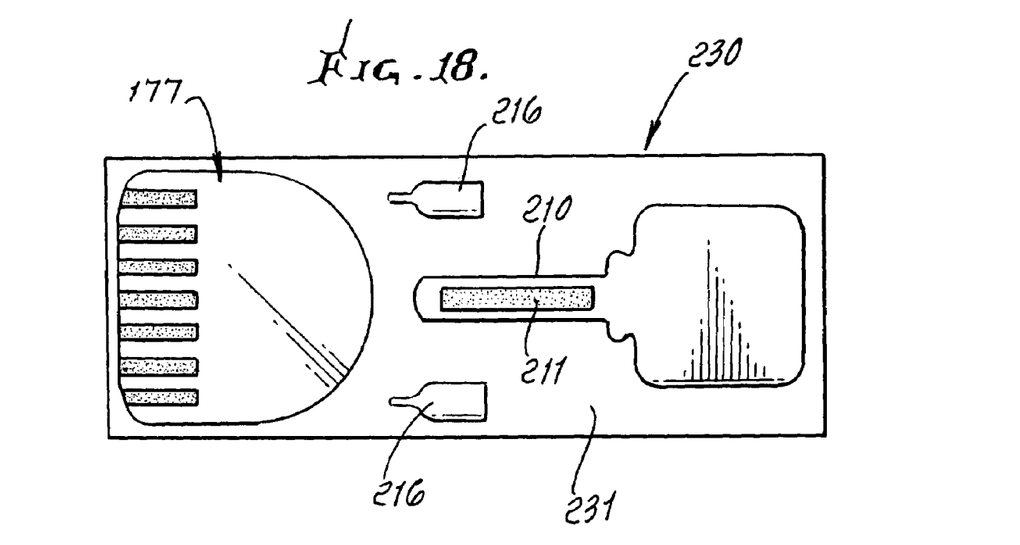
FIG. 18 shows a kit embodying probe, ampule and calorimeter elements.

FIG. 18 shows a kit 230 including a carrier tray 231; probe 210 on the tray; and hydroxide ampules 216 on the tray; and a pH color comparison chart 177 on the tray. That type chart use also referenced in FIG. 11. Elements of the kit are used as described in FIGS. 15-17, after removal from the tray.

In the above, the word "hydroxide" is intended to include, within its scope, alkaline substances, that may for example be flowable.

Figure 20A:
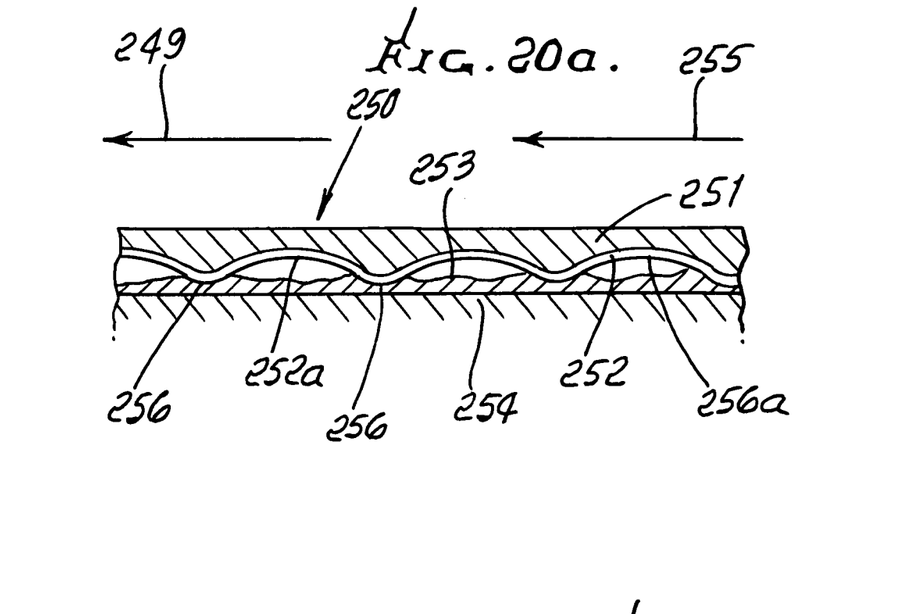
FIG. 20a is an enlarged fragmentary view showing a preferred multiple crested indicator positioned for gathering of vaginal moisture, as from a layer.
Figure 20B:
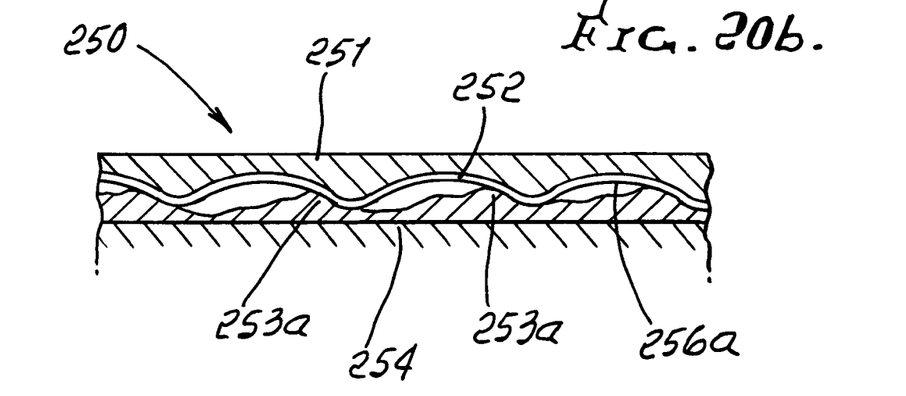
FIG. 20b is like FIG. 20a, but showing the indicator moved or moving relative to the vaginal moisture being gathered.
Figure 20C:
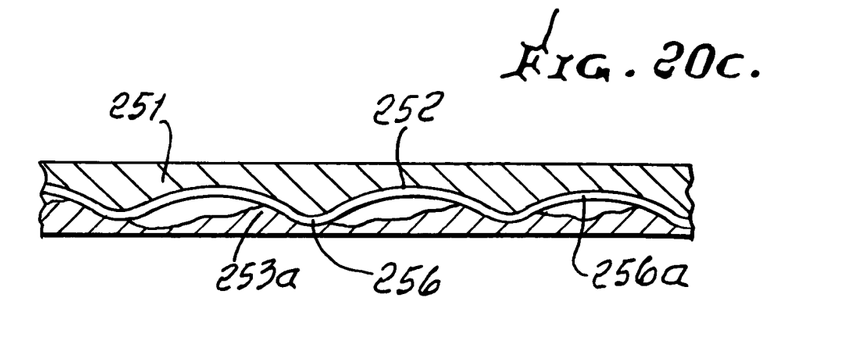
FIG. 20c shows the moisture gathered by the indicator, and externally of the vagina, for test purposes as in FIG. 17.

Referring to FIGS. 20a, 20b and 20c, a manipulable element 250 includes a probe 251, elongated in direction 249, and which is sized to be insertable into the vagina. An indicator 252, such as a strip of material, is provided on a side of the element or probe, and may comprise an amine indicator. The indicator has an outer surface 252a to be exposed to vaginal moisture 253 as may reside at a wall 254 of the vagina. The indicator surface presents a sequence of widthwise extending crests 256 confronting wall 254 and moisture thereon or thereat, and operable to collect moisture between the crests, as at 253a in FIG. 20b, in response to manipulated movement of the element or probe, and indicator 252, in the general lengthwise direction 255. Such movement, and positioning of the crested indicator, effects collection of the moisture, to be concentrated as at 253a between the crests, as at zones or valleys 256a defined by the indicator, between the crests. See FIG. 20c. As a result, when the probe or element is removed endwise from the vagina, the moisture concentrations, or parts thereof, tend to remain in zones 256a, adherent to the zone or valley surfaces between the crests, and presence of amine in response to hydroxide contact with the moisture concentrations, can be readily detected, as by the whiff test referred to.

Figure 20D:
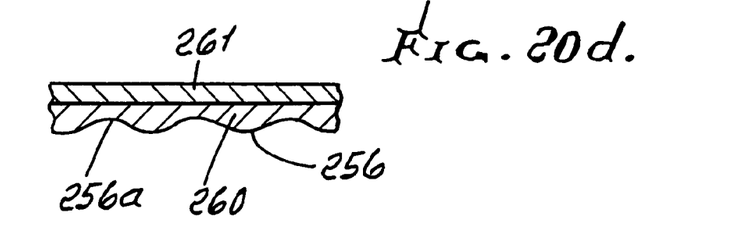
FIG. 20d shows a modification.

FIG. 20d shows the indicator strip 260 adherent to a flat surface 261 of the probe; the strip itself forming the crests 256 and valleys 256a.

If the wavy surface of the probe itself is utilized as an indicator, collected moisture resides in the intermediate zones or valleys between crests in FIG. 20d. Hydroxide may then be applied to the collected moisture, externally of the vagina, for the amine test.

Figure 20E:
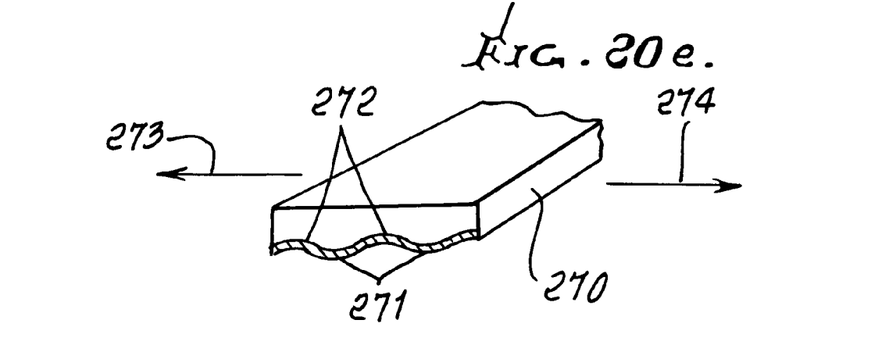
FIG. 20e shows another modification.

FIG. 20e shows a modified probe 270 having longitudinally elongated extending crests 271 and a valley or valleys 272 between those crests. The crests and valleys may be on indicator paper or material, or on the probe surface, as referred to above. The probe 270 can be moved laterally in directions 273 and 274, i.e. as with scooping action, to collect vaginal wall moisture in valleys or troughs 272.

Figure 19:
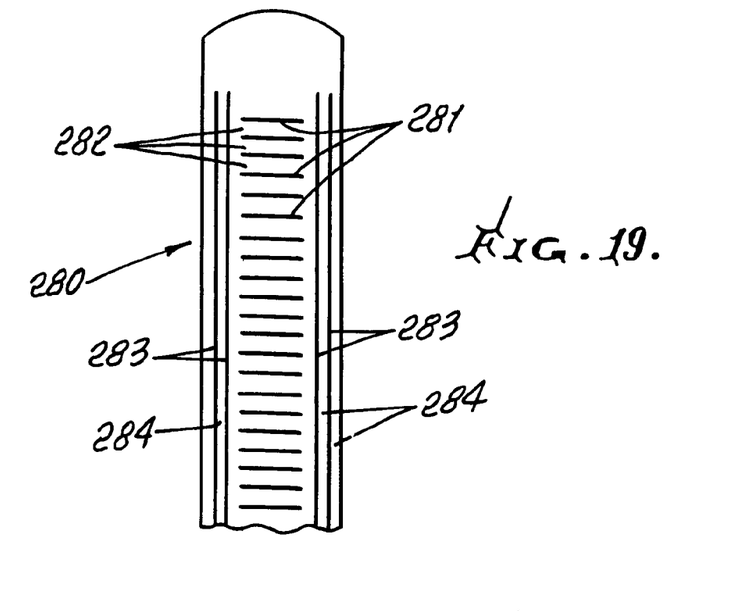
FIG. 19 shows a modified elongated moisture gathering probe.

FIG. 19 shows a modified elongated probe 280 having both widthwise extending crests 281 and valleys 282 between 281, lengthwise extending crests 283 and valleys 284 between 283. This enables moisture collection in valleys or troughs 282 as the probe is moved lengthwise, normal to crests 281 and moisture collection in valleys or troughs 284 as the probe is moved externally or sideways, in the vagina, normal to crests 283. Crests 283 also act to block lateral escape of moisture from valleys 282. FIG. 19 may be regarded as preferred, for moisture collection in response to probe movement both longitudinally and laterally.

It will be noted in the above that the valleys between successive crests have depths which are typically substantially less in dimension than the spaces between successive crests.

Also, the probe itself may consist of biodegradable material, to self destruct after use.

In the above, the probe element is provided to include an enlarged substantially flat handle from which the probe projects longitudinally to be gripped between the user's thumb and forefinger, the handle having two laterally shaped edges presented toward said pH indicator and spaced generally longitudinally therefrom to limit probe longitudinal insertion into the vagina, said pH indicator aligned on a line which extends between said two edges, and said pH indicator having curved edges facing oppositely and convexly away from said line, and protruding at opposite edges of said probe, said handle edges also presented toward said crests, as disclosed.

I claim:

1. Apparatus for quick screening for vaginal moisture pH level and for amine associated with such moisture, comprising
   a) a manipulable element including a probe insertable into the vagina,
   b) a pH indicator on a first side of said element, said indicator characterized as producing a color which corresponds to pH level of vaginal moisture contacting the indicator,
   c) and a second indicator on a second side of said element, said second indicator elongated lengthwise of said element and being an amine indicator,
   d) said second indicator having an outer surface exposed to vaginal moisture, said surface presenting a sequence of crests for collection of said moisture between said crests in response to movement of the element in the vagina, and wherein said crests extend generally widthwise and lengthwise of the second indicator, said lengthwise extending crests being spaced apart from one another widthwise of the probe and bridging ends of multiple of the widthwise extending crests along the probe length, the lengthwise extending crests spaced from said ends of the widthwise extending crests, said widthwise extending crests having outwardly presented wavelike convex surfaces extending laterally crosswise of the probe, the probe having lateral width substantially exceeding probe thickness, e) said indicators having generally the same sizes and shapes, f) said element including a handle from which the probe projects longitudinally so that the handle may be gripped manually, the handle having two laterally spaced and shaped edges presented toward the indicators, and spaced generally longitudinally therefrom to limit probe longitudinal insertion into the vagina, said indicators being aligned with respect to a line which extends longitudinally between said two edges, and the probe proximate both the indicators having curved edge portions facing convexly away from said line, and protruding at opposite edges of the probe.

2. The apparatus of claim 1 wherein there are valleys located between said crests on the second indicator, the valleys having outwardly presented shallow concave surfaces, between the crests.

3. The apparatus of claim 2 wherein the valleys have depths which are substantially less in dimension than the spacing between successive crests.

4. The apparatus of claim 2 wherein said crests and valleys define said surface as undulating.

5. The apparatus of claim 1 wherein said second indicator is a strip of material adherent to said probe and defining said surface as undulating.

6. The method of quickly screening for vaginal moisture pH level as it relates to a pre-selected pH level, that includes the steps:

a) providing a manually manipulable element including a probe insertable into the vagina, b) providing a pH indicator on said element, said indicator characterized as producing a color which corresponds to pH level of vaginal moisture contacting the indicator, c) and providing a second indicator on another side of said element, said second indicator being elongated lengthwise of the element and being an amine indicator, d) said second indicator provided to have an outer surface exposed to vaginal moisture, said surface presenting a sequence of crests for collection of said moisture between said crests in response to movement of the element in the vagina, e) and wherein said element is provided to include an enlarged substantially flat handle from which the probe projects longitudinally to be gripped between the user's thumb and forefinger, the handle having two laterally shaped edges presented toward said pH indicator and spaced generally longitudinally therefrom to limit probe longitudinal insertion into the vagina, said pH indicator aligned on a line which extends between said two edges, and said pH indicator having curved edges facing oppositely and convexly away from said line, and protruding at opposite edges of said probe, said handle edges also presented toward said crests, f) said crests having outwardly presented wavelike convex surfaces extending laterally crosswise of the probe, the probe having lateral width substantially exceeding probe thickness.

7. The method of claim 6 including using said element to collect vaginal moisture on said surface between said crests, as the element is moved generally normal to the crests.

8. The method of claim 7 including thereafter, externally of the vagina, applying an hydroxide to the moisture collected between the crests, thereby to produce an amine, and detecting the presence of said amine.

9. The method of claim 6 wherein the probe is manipulated both longitudinally and laterally, in the vagina to effect said collection.

10. The method of claim 6 including also enabling vaginal moisture pH determination in connection with said probe manipulation.

11. The method for quick screening for vaginal moisture pH level and for amine associated with such moisture, that includes the steps:

a) providing a manipulable element including a probe insertable into the vagina, b) providing a pH indicator on a first side of said element, said indicator characterized as producing a color which corresponds to pH level of vaginal moisture contacting the indicator, c) providing a second indicator on a second side of said element, said second indicator elongated lengthwise of said element and being useful as an amine indicator, d) and providing said second indicator with an outer surface exposed to vaginal moisture, said surface presenting a sequence of crests for collection of said moisture between said crests in response to movement of the element in the vagina, e) and wherein said element is provided to include an enlarged substantially flat handle from which the probe projects longitudinally to be gripped between the user's thumb and forefinger, the handle having two laterally shaped edges presented toward said pH indicator and spaced generally longitudinally therefrom to limit probe longitudinal insertion into the vagina, said pH indicator aligned on a line which extends between said two edges, and said pH indicator having curved edges facing oppositely and convexly away from said line, and protruding at opposite edges of said probe, said handle edges also presented toward said crests, f) said crests having outwardly presented wavelike convex surfaces extending laterally crosswise of the probe, the probe having lateral width substantially exceeding probe thickness.

12. The method of claim 11 including manipulating said probe to effect collection of vaginal moisture concentrations on said second indicator outer surface and between said surface crests.

13. The method of claim 12 including thereafter, externally of the vagina, applying an hydroxide to said second indictor surface, and detecting presence of an amine or amines produced at said second indicator.

14. The method of claim 11 wherein said first and second sides are at opposite sides of the probe.

15. The method of claim 11 including providing a carrier for said hydroxide, and manipulating said carrier to effect said application of the hydroxide to said second indictor surface.

16. The method of claim 15 wherein said hydroxide carrier is provided in the form of an ampule.

17. The method of claim 11 wherein said crests are provided to extend generally widthwise or lengthwise of the second indicator.

18. The method of claim 11 wherein said crests are provided to extend generally widthwise and lengthwise of the second indicator.

19. The method of claim 11 wherein valleys are provided between said crests.

20. The method of claim 19 wherein the valleys have depth which are substantially less in dimension than the spacing or spacings between successive crests.

21. The method of claim 19 wherein such crests and valleys are provided to form said surface as undulating.

22. The method of claim 11 wherein said second indicator is provided in the form of a strip of material adherent to the probe, said surface formed as undulating in the direction of probe manipulated movement in the vagina.

23. The method for quick screening for amine associated with vaginal moisture, that includes the steps
   a) providing a manipulable element including a probe insertable into the vagina,
   b) providing an indicator on a side of said probe, and being an amine indicator,
   c) said indicator having an outer surface exposed to vaginal moisture, said surface presenting a sequence of crests for collection of said moisture between said crests in response to movement of the element in the vagina,
   d) and wherein the crests extend generally widthwise and lengthwise of the indicator, said lengthwise extending crests being spaced apart from one another widthwise of the probe and bridging ends of multiple of the widthwise extending crests along the probe length, the lengthwise extending crests spaced from said ends of the widthwise extending crests,
   e) the widthwise extending crests having outwardly presented wavelike convex surfaces extending laterally crosswise of the probe, the probe having lateral width substantially exceeding probe thickness,
   f) providing a second indicator on said probe,
   g) said indicators having generally the same sizes and shapes,
   h) said element including a handle from which the probe projects longitudinally so that the handle may be gripped manually, the handle having two laterally spaced and shaped edges presented toward the indicators, and spaced generally longitudinally therefrom to limit probe longitudinal insertion into the vagina, said indicators being aligned with respect to a line which extends longitudinally between said two edges, and the probe proximate both the indicators having curved edge portions facing convexly away from said line, and protruding at opposite edges of the probe.

24. The method of claim 23 including manipulating said probe to effect collection of vaginal moisture concentration on said indicator outer surface, and between said crests.

25. The method of claim 24 including thereafter, externally of the vagina, applying an hydroxide to said second indictor surface, and detecting presence of an amine or amines produced at said second indicator.

26. The method of claim 25 wherein the valleys have depths which are substantially less in dimension than the spacing or spacings between successive crests.

27. The method of claim 23 wherein said crests are provided to extend generally widthwise or lengthwise of the second indicator.

28. The method of claim 23 wherein said crests are provided to extend generally widthwise and lengthwise of the second indicator.

29. The method of claim 23 wherein valleys are provided between said crests.

30. The method of claim 23 wherein said second indicator is provided in the form of a strip of material adherent to the probe, said surface formed as undulating in the direction of probe manipulated movement in the vagina.

31. Apparatus for quick screening for vaginal moisture pH level and for amine associated with such moisture, comprising
   a) a manipulable element including a probe insertable into the vagina,
   b) a pH indicator on a first side of said element, said indicator characterized as producing a color which corresponds to pH level of vaginal moisture contacting the indicator,
   c) and a second indicator on a second side of said element, said second indicator elongated lengthwise of said element and being an amine indicator,
   d) at least one of said indicators having an outer surface exposed to vaginal moisture, said surface presenting a sequence of crests for collection of said moisture between said crests in response to movement of the element in the vagina,
   e) and wherein said crests extend generally widthwise and lengthwise of the second indicator, said lengthwise extending crests being spaced apart from one another widthwise of the probe and bridging ends of multiple of the widthwise extending crests along the probe length, the lengthwise extending crests spaced from said ends of the widthwise extending crests,
   f) said crests having outwardly presented wavelike convex surfaces extending laterally crosswise of the probe, the probe having lateral width substantially exceeding probe thickness,
   g) said indicators having generally the same sizes and shapes,
   h) said element including a handle from which the probe projects longitudinally so that the handle may be gripped manually, the handle having two laterally spaced and shaped edges presented toward the indicators, and spaced generally longitudinally therefrom to limit probe longitudinal insertion into the vagina, said indicators being aligned with respect to a line which extends longitudinally between said two edges, and the probe proximate both the indicators having curved edge portions facing convexly away from said line, and protruding at opposite edges of the probe.

32. The apparatus of claim 31 wherein the crests extend generally widthwise or lengthwise of the second indicator.

33. The apparatus of claim 31 wherein the crests extend generally widthwise and lengthwise of the second indicator.

34. The apparatus of claim 31 wherein there are valleys located between said crests on the second indicator.

35. The apparatus of claim 34 wherein the valleys have depths which are substantially less in dimension than the spacing between successive crests.

36. The apparatus of claim 34 wherein said crests and valleys have depths which are substantially less in dimension than the spacing between successive crests.

37. The apparatus of claim 34 wherein said crests and valleys have depths which are substantially less in dimension than the spacing between successive crests.

* * * * *